(12) United States Patent
Takehara et al.

(10) Patent No.: US 7,267,239 B2
(45) Date of Patent: Sep. 11, 2007

(54) METHOD FOR NONINTRUSIVE SCANNING OF CARGO CONTAINERS IN A BUFFER OPERATION

(76) Inventors: Toru Takehara, 19 Del Monte Pl., San Mateo, CA (US) 94403; Kinya Ichimura, 854 Andromeda La., Foster City, CA (US) 94404; Sun Huan Huang, 35150 Arbordale Ct., Fremont, CA (US) 94536; Philip Alexander Tam, 6400 Christie Ave., Emeryville, CA (US) 94608

(*) Notice: Subject to any disclaimer, the term of this patent is extended or adjusted under 35 U.S.C. 154(b) by 88 days.

(21) Appl. No.: 10/639,956

(22) Filed: Aug. 12, 2003

(65) Prior Publication Data
US 2005/0036853 A1    Feb. 17, 2005

(51) Int. Cl.
*G01N 23/04* (2006.01)

(52) U.S. Cl. .................. 212/270; 212/325; 378/57; 414/140.3

(58) Field of Classification Search ........... 212/270, 212/271, 325; 378/57; 414/140.3
See application file for complete search history.

(56) References Cited

U.S. PATENT DOCUMENTS

| | | | | |
|---|---|---|---|---|
| 3,247,974 A | * | 4/1966 | Dechantsreiter | 414/591 |
| 3,547,277 A | * | 12/1970 | Strayer | 212/317 |
| 3,812,987 A | * | 5/1974 | Watatani | 414/561 |
| 6,768,421 B1 | * | 7/2004 | Alioto et al. | 340/600 |
| 6,778,631 B2 | * | 8/2004 | Franke | 378/57 |
| 6,845,873 B1 | * | 1/2005 | Chattey | 212/270 |
| 2004/0156477 A1 | * | 8/2004 | Bjorkholm | 378/146 |

FOREIGN PATENT DOCUMENTS

WO      2004/085298      *    1/2004

* cited by examiner

*Primary Examiner*—Thomas J. Brahan
(74) *Attorney, Agent, or Firm*—Bruce & McCoy; Ernest H. McCoy

(57) ABSTRACT

A method for nonintrusive scanning of cargo containers quay side while the containers are being transferred between ship and land transportation utilizing a mobile cargo container handling buffer crane having a bridge crane mounted thereon for transferring cargo containers between a ship and land transportation with an intermediate transfer position whereby a suspended container can be noninvasively inspected by a longitudinally reciprocating container traversing radiation emitter apparatus.

2 Claims, 4 Drawing Sheets

METHOD FOR NONINTRUSIVE SCANNING OF CARGO CONTAINERS IN A BUFFER OPERATION

CROSS REFERENCES TO RELATED APPLICATIONS

The present invention is related to assignees' U.S. Pat. No. 6,604,904, issued Aug. 12, 2003, for Method for Buffer Crane Operation in Cargo Container Handling and passed to allowance May 7, 2003. The present invention is also related to the assignees' U.S. Pat. No. 6,602,036, issued Aug. 5, 2003, for Buffer Bridge Crane for Cargo Container Handling Operations and also passed to allowance May 7, 2003. These patent disclosures are incorporated herein by reference.

BACKGROUND OF THE INVENTION

1. Field of the Invention

The present invention relates to a method primarily for the purpose of nonintrusive scanning of cargo containers for nuclear based weapons which is intended for use during container transfer between a ship and land transportation.

More particularly it relates to a buffer crane having radiation emission scanning apparatus arranged for nonintrusive interrogation or inspection of cargo containers while each container is being transferred between a ship and quay side land transportation without slowing the quay crane container transfer cycle.

Still more particularly, the present invention is a method of operation of a mobile cargo container buffer and scanning crane which transfers cargo containers between land transportation and a quay crane pickup buffer position and which suspends the cargo container being transferred at a predetermined inspection position for radiation emission examination by a craneboard apparatus before depositing the cargo container at the intended transfer buffer deposition position.

Specifically it relates to a method of operation of a mobile platform having a bridge crane mounted thereon for transferring cargo containers between either a quay crane pickup position, or quay side land transportation, and a predetermined inspection position on said platform where it can be non-intrusively inspected by a longitudinally reciprocating radiation emission inspection apparatus while functioning as a buffer operation. The container is then either deposited on land transportation such as a truck trailer chassis or deposited on the buffer position for pickup by a quay crane for transfer to a ship.

2. Description of the Prior Art

In view of recent terrorist activities throughout the world, considerable effort is being given by analysts to improving security measures with respect to the maritime industry and United States port operations. At the present time, based on the Automated Tracking System, an intelligence based search system used by U.S. Customs, it has been estimated that the probability that contraband will be discovered in containers that are entering the U.S. is less than 50 percent. Thus, the maritime industry provides a delivery system for weapons of mass destruction and every other container could possibly conceal an atomic weapon which, if exploded in a U.S. port, in addition to causing massive destruction, would essentially end international trade.

The methods to be employed to improve U.S. port security may prove severely detrimental to port productivity. The ideal performance standard is 100 percent inspection of inbound containers to U.S. ports. Apart from physically unloading and inspecting the contents of every container, the obvious alternative is to non-intrusively inspect each container such as by x-ray and when more sophisticated means of nonintrusive inspection are developed, such as gamma ray scanning and neutron analysis, implementing the use of those developments in addition to x-ray based systems.

The use of x-ray machinery in one manner or another for the purpose of inspecting containers is discussed in the prior art literature. However, despite the numerous designs, structures, and forms of apparatus disclosed by the prior art, which have been developed for the accomplishment of the specific objectives, purposes, and requirements of container contents inspection, the devices, machines, and methods which have been hereto for suggested to accomplish these goals consist basically of familiar, expected, and obvious, configurations, combinations, and arrangements of apparatus. However, these designs have essentially added processing steps to port operations, and the size is of the machinery and complexity of the processing steps essentially interrupted the established system of port operations. This factor causes problems when attempting to integrate the technology into cargo container handling.

The problem with instituting high-energy x-ray scanners for cargo container examination, apart from safety concerns, is that the equipment will reduce port productivity by disrupting highly developed port operations and consuming valuable terminal space. The primary disadvantage is the interruption of the cargo container transfer process between ship and shore. Most importantly, it interferes with the quay crane offloading cycle time which is crucial to a ship's berthing time at the dock which must be kept at a minimum.

The inspection procedure requires holding a container immobile so that it can be x-rayed. While the cycle times for the x-ray process may ultimately be reduced over time by improved technology, all of the presently considered means for effecting the x-ray process require either stopping the container movement for processing (usually during unloading in U.S. ports and, if required, in loading at foreign ports) or multiple additional handling steps of the container during the transfer process by taking it out of the normal handling cycle, and to an extra handling step, at an x-ray position for processing, and then returning the container into the transfer cycle.

The present invention permits integration of the x-ray process into the buffer station method of crane operation disclosed in the prior patented related apparatus and methods of buffer crane operation whereby the inspection process can occur concurrently during the cargo container transfer between ship and shore without interruption of the quay crane transfer cycle.

The mobile cargo container scanning crane contemplated according to the present invention departs substantially from the conventional concepts and designs contemplated by the technical literature, and in doing so, provides an apparatus primarily developed for the purpose of nonintrusive cargo container inspection during transfer between ship and shore as described above, but it accomplishes the result in a different and improved manner for producing a transfer cycle with a buffer inclusive procedure for container inspection which is easily integrated into the container transfer cycle for faster processing times and more efficient port operation.

SUMMARY OF THE INVENTION

In view of the foregoing known and obvious disadvantages inherent in the known types and methods of container inspection presently utilized in the port operations, the present invention provides a new method, apparatus, and construction for integrated cargo container inspection during ship and shore container transfers wherein the same can be utilized to maintain port efficiency.

The general purpose of the present invention, which will be described hereafter in greater detail, is to provide a new and improved cargo container inspection apparatus which has many of the vantages of the prior art of container inspection mentioned and described above and many novel features and advantages that result in a new integrated to container transfer cycle which is not anticipated, rendered obvious, suggested, or even implied by any of the prior art of container inspection and heretofore known, either alone or in any combination thereof.

The present invention is a method for nonintrusive scanning of cargo containers quay side while they are being transferred between ship and land transportation without interrupting the ship loading or unloading cycle operations. The steps comprise providing a mobile scanning platform which can be position under a quay crane whereby containers can be deposited on two or remove from the platform by a quay crane. The platform is provided with a container listing apparatus for transferring containers between a landing position on the platform and truck trailer chassis located below or alongside the platform. The listing apparatus is capable of suspending the container and a predetermined position with respect to the platform and a mobile scanning inspection apparatus is provided on the platform capable of traversing the length of the platform. The container said then scan during transfer between the truck trailer chassis and the landing position on the platform while containers are suspended at the predetermined position.

The more important features of the invention have been broadly outlined in the preceeding summary of the invention in order that the detailed description thereof which follows may be better understood and in order that the present contribution to an improvement in the art may be better appreciated. There are additional features of the invention that will be described hereinafter and which will form the subject matter of the claims appended hereto.

With respect to the claims hereof, and before describing at least one preferred embodiment of the invention in detail, it is to be understood that the invention is not to be limited in its application to the details of construction and to the arrangements of the components which are set forth in the following description or illustrated in the accompanying drawings. The invention is capable of being created in other embodiments and of being practiced and carried out in various ways. Also, it is to be understood that the phraseology and terminology employed here are for the purpose of description and should not be reguarded as limiting.

As such those skilled in the art in which the invention is based will appreciate that the conception upon which this disclosure is predicated may readily be utilized as a basis for the designing of other forms, structures, apparatus, systems, and methods for carrying out the several purposes of the present invention. It is important, therefore, that the claims be regarded as including such equivalent constructions in so far as they do not depart from the spirit and scope of the present invention.

Further, the purpose of the appended abstract is to enable the United States Patent and Trademark Office, and the public generally, and especially scientists, engineers and practitioners of the art who are not familiar with the patent and legal terms or phraseology, to determine quickly from cursory inspection the nature and essence of the technical disclosure of the application. The abstract is neither intended to define the invention of the specification, which is measured by the claims, nor is it intended to be limiting as to the scope of the invention in any way.

OBJECTS OF THE INVENTION

It is therefore an important object of the present invention to provide a method for nonintrusive inspection of cargo containers.

It is another object of the present invention to provide a method for nonintrusive of cargo containers which is integrated into the transfer cycle of a cargo container between ship and shore.

It is a further object of the present invention to provide a mobile crane which transfers be cargo container between a buffer station and land transportation and has an intermediate position for radiation emitter inspection during the buffer mode of operation.

It is still another object of the present invention to provide a mobile crane which carries longitudinally reciprocating x-ray apparatus for inspecting cargo containers suspended by said crane.

And it is yet a further object of the present invention to provide a mobile crane which integrates cargo container transfers between land transportation and a buffer station for pickup by a quay crane with nonintrusive inspection of the cargo containers while they are suspended by the crane during transfer between the two positions.

Other objects and advantages of the present invention will become apparent when the description of the method of the present invention is considered in conjunction with the accompanying drawings.

DESCRIPTION OF THE PREFERRED EMBODIMENT

Reference is made to the drawings for a description of the preferred embodiment of the present invention wherein like reference numbers represent like elements on corresponding views.

Figure 1:
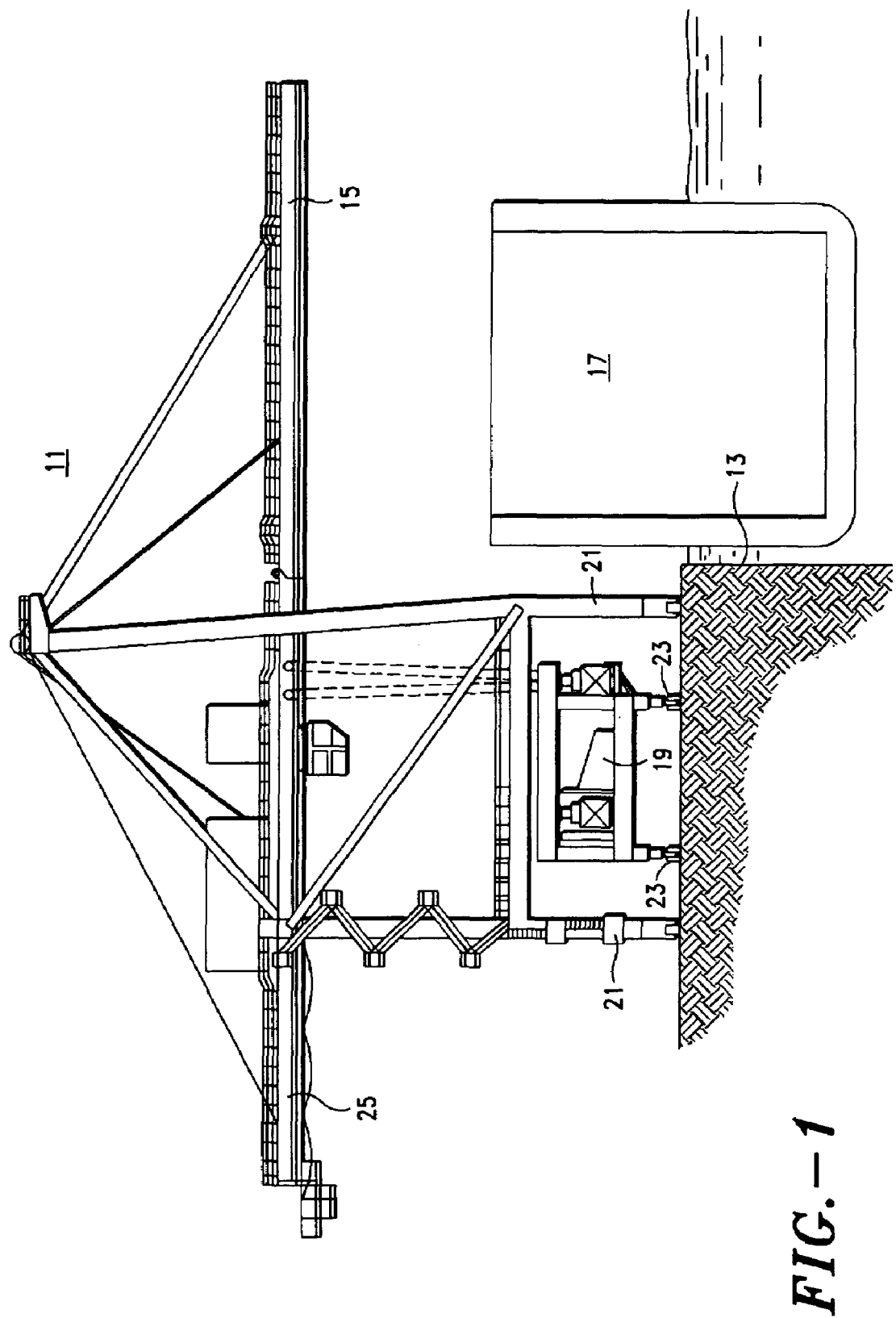
FIG. 1 is a side elevation of a typical quay crane with a scanning crane of the present invention located thereunder.

Reference is made to FIG. 1 of the drawings which shows a typical container handling quay crane 11 located dockside in a shipping port. It is mounted on rails disposed parallel to the dock edge 13. The quay crane traverses the wharf to position itself to project its cantilevered boom 15 over the rows of container cells of the adjacently berthed ship 17 when the boom is lowered. The scanning bridge crane 19 of the present invention is shown disposed below the quay crane between the support legs 21. It is mounted on pneumatic tires 23 for independent movement on the wharf whereby it can be located at variable positions below or adjacent to the quay crane: either between the support legs or alongside under a cantilevered shoreside back reach 25.

The scanning crane 19 is a low-profile buffer crane which can be positioned underneath a quay crane 11 between its support legs 21 during container handling operations. It is contemplated that a buffer/scanning crane could also be utilized in a railroad stacking yard, under a large bridge or straddle crane, as well as dockside, so the term "quay crane" as used in the claims to describe the environment of the invention is intended to include these and other types of container storage yard and railyard container handling cranes as well.

The method for nonintrusive scanning of cargo containers quay side, taught by the present invention, accomplishes the task while the containers are being transferred between ship and land transportation without interrupting the ship loading or unloading cycle operations. The method includes providing a mobile scanning platform which can be positioned under a quay crane whereby the containers can be deposited on to or removed from the platform during a buffer operation by a quay crane.

Figure 2:
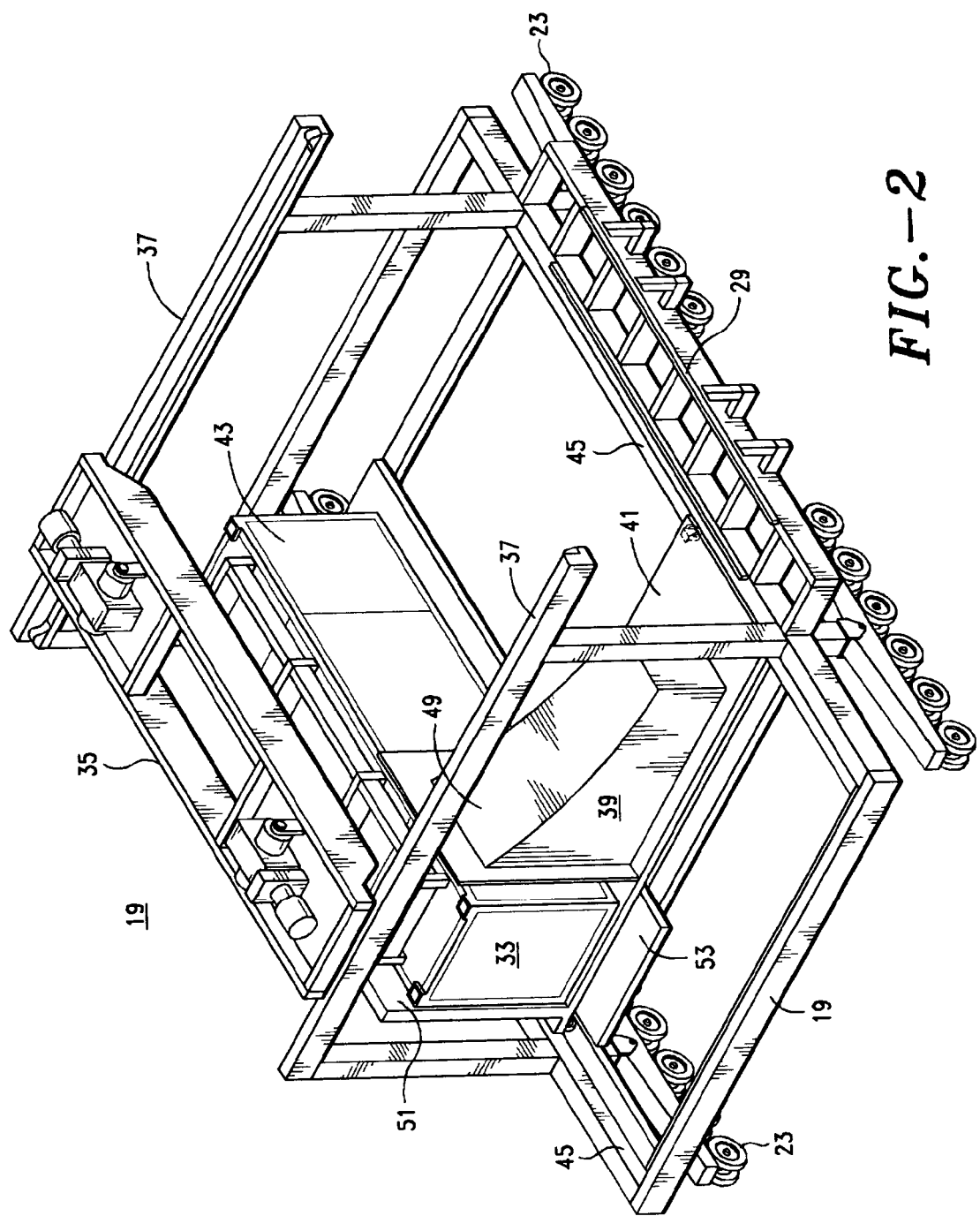
FIG. 2 is a is a perspective view of the scanning crane of the present invention shown in operation.
Figure 3:
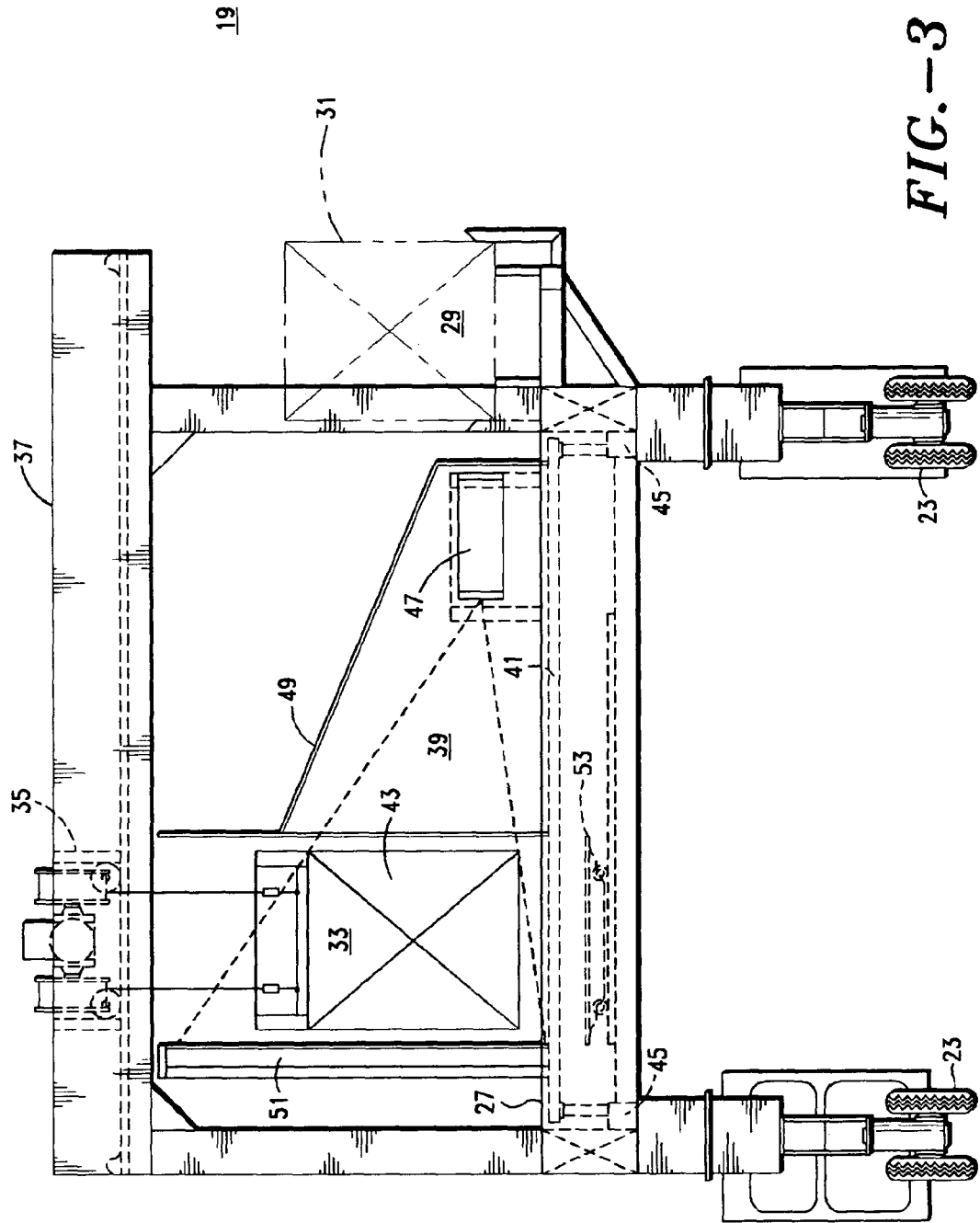
FIG. 3 is a is an end view of FIG. 2.
Figure 4:
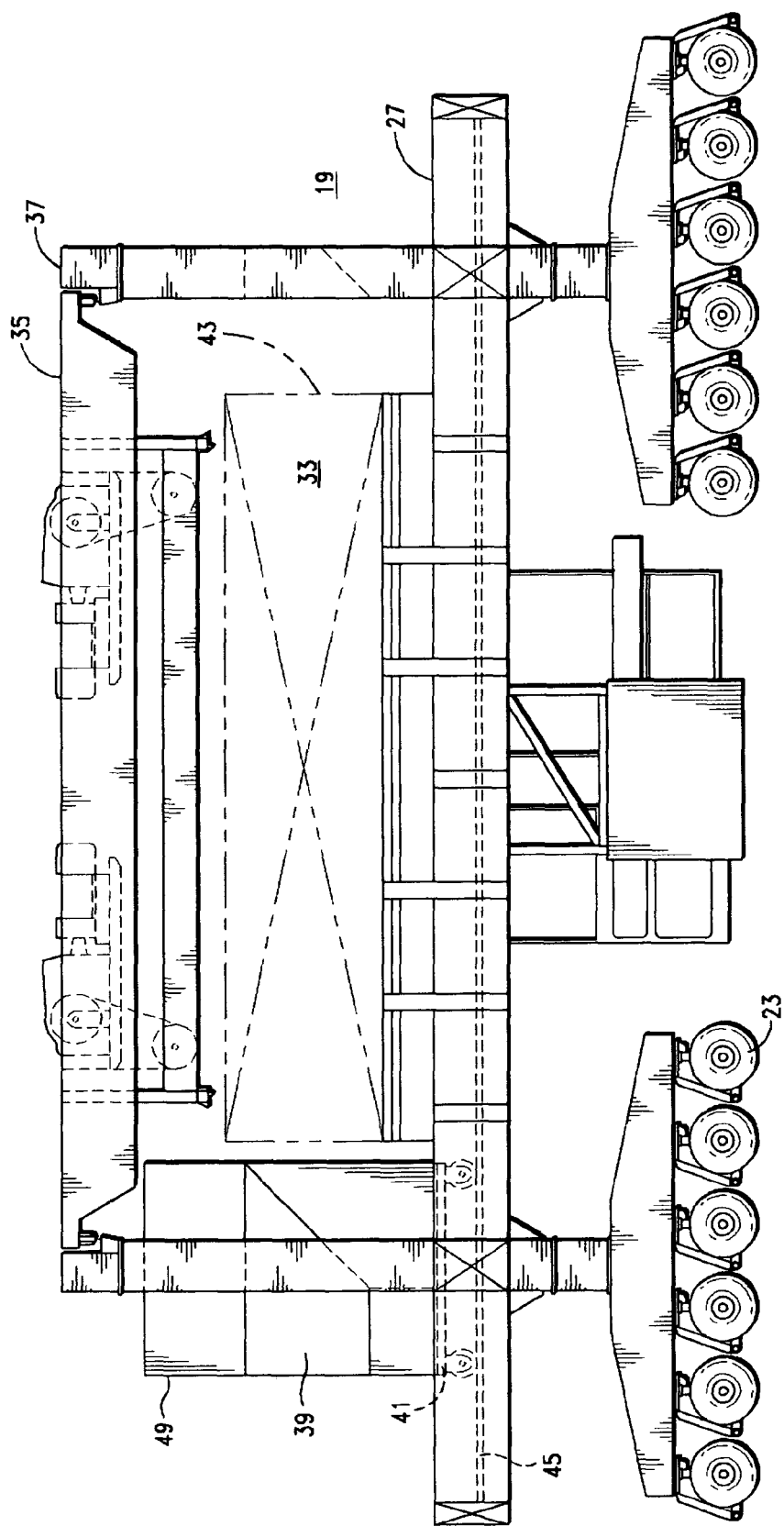
FIG. 4 is a is a side elevation of FIG. 2.

Reference is made to FIGS. 2-4 which disclose a mobile cargo container buffer/scanning bridge crane 19 in operation as contemplated by the present invention. The crane is comprised of a multiple tire 23 or a wheel supported platform 27 having a floor and formed for independent movement in a quay area. It is essentially a landing deck mounted on legs so that container transporters can pass underneath. Containers can be landed on the deck and temporarily stored by a quay crane when they are removed from shipboard or where containers picked off ground level transporters can be landed and stored until they are picked up by the quay crane for transport to a ship. The landing deck can thereby function as a buffer crane quite effectively and even more so when constructed with multiple landing positions for containers as described in the patents described supra and incorporated herein.

The first step of the method comprises providing a mobile scanning platform having one or more container landing positions for buffer operation which can be positioned under a quay crane whereby containers can be deposited onto or remove from the platform by a quay crane.

The second step of the method comprises providing the platform with a container lifting apparatus for transferring containers between a first predetermined landing position on the platform and a third predetermined positioned located below or alongside the platform. It lifting apparatus is capable of positioning a container and a second predetermined positioned with respect to the platform between the first and third predetermined positions.

The landing deck or platform 27 has a first predetermined position 29 for the deposit of containers 31 which have been offloaded from a ship by a quay crane or where containers being transferred from land transportation can be landed until picked up by the quay crane for transfer to a ship. This first predetermined position is labeled the "first" for designation purposes and does not necessarily describe its position as a sequence step in container transfer operations except in the one specific mode of crane operation: ship to shore transfer. Conversely, it is the last predetermined position in a shore to ship container transfer. Therefore, the designation as a first position is an arbitrary selection simply because the most immediate need in the industry is for inspection of containers being landed in the United States, and that sequence starts with the quay crane landing the container first on the buffer deposition position of the scanning crane.

This first predetermined position 29 can actually be comprised of a number of landing positions for the temporary storage of containers during ship loading and unloading operations whereby the scanning crane 19 can also function as a buffer crane as taught by the related and incorporated patents although a single buffer deposition position can be sufficient under some conditions for the scanning crane to function adequately as a buffer crane.

The scanning/buffer crane 19 has a second predetermined position 33 which, in the preferred embodiment of the invention, is a suspended position where a container is held for nonintrusive examination. It can also be a landing position depending upon the type of scanning apparatus which is employed.

In terms of relative time, the scanning crane 19 can remain engaged to or hold onto a container being transferred between ship and shore for a reasonably long period of time during the transfer operations in relation to the cycle time of the quay crane 111 in order to accomplish the inspection/interrogation on a container.

The quay crane 11 requires time to engage a container, either on shipboard in a container cell, or shoreside from a dockside transporter or a buffer crane, and then to lift the container to shipboard clearance height while translating it horizontally between ship and shore, and then for lowering the container to an accurate deposition height and position for release either in a shipboard cell or onto a predetermined position on a buffer crane or onto a ground transporter. This quay crane transfer cycle time involves considerably more time than the scanning crane needs to engage a container, to lift and move it a short distance into inspection position, take the necessary time to scan it, and to deposit it at the predetermined release position. As a result, the scanning crane, when functioning in a buffer operation, can perform the scanning operation without interrupting the quay crane cycle times. The related patents, supra, disclose a buffer crane which includes multiple landing/storage positions to ensure that a fully functional buffer operation is achieved, but even a single buffer container landing position on a scanning crane will be sufficient for performing a buffer operation in those cases where the quay crane transfer cycle times are sufficiently slow.

A bridge crane 35 is mounted on a pair of leg supported crossbeams 37 above the mobile platform and generally spans the length of the cargo containers it is intended to handle. It is arranged for engaging either a cargo container mounted on a truck trailer chassis disposed either below or alongside the platform at the third predetermined position or for depositing a container thereonto. The bridge crane lifts or lowers the containers between the third and second predetermined positions through an opening in the floor of the landing deck. In those situations where the clearance height under the crossmembers extending between the legs of a quay crane is limited, it may not be possible to drive container transporters under the scanning crane. In that case, it would be necessary to lift or deposit containers from and to transporters parked alongside the scanning crane. To do so, the support rails for the bridge crane on the crossbeams 37 would be extended to project laterally over the adjacent truck parking positions with cantilevered beam projections.

The bridge crane 35 is formed for raising a container from a trailer chassis to the platform height at the second predetermined position which is disposed at one side of the platform. Is also formed for moving horizontally and translating a container to the first predetermined container landing position(s) and depositing it thereon. In other words, the bridge crane moves containers between land transportation (third predetermined position) and the quay crane landing positions (first predetermined position) with an intermediate container hold position (second predetermined position) for container examination during the transfer cycle. The second predetermined position in the preferred embodiment of the invention is a suspended position, usually above the third predetermined position. However, it could be a deposition position most likely on the level of the first predetermined position as will be described.

In a subsequent step of the method, the platform is provided with a container scanning inspection or interrogation apparatus 39 mounted on the platform 27 and formed for reciprocating longitudinal movement on a trolley 41 above the platform to traverse the length of a cargo container 43 and suspended by the bridge crane 35 at the second predetermined position 33. It is mounted on a wheeled trolley which runs on rails 45 that extend for substantially the length of the platform. The second predetermined position could be a deposition position on the front of the scanning apparatus support platform.

The scanning apparatus 39 can be provided with a hold or rest position at one end of the platform as shown in FIG. 4 to permit the vertical transfer of containers between the second and third predetermined positions without mechanical interference. Such a hold position for the scanning apparatus may not be necessary. As presently envisioned, due to the physical construction and space requirements of presently available and utilized scanning apparatus, the reciprocating and translating platform 41 is mounted on tracks 45 so it can slide from one end of a container 43, suspended at the second predetermined position 33, to the other. In all likelihood, the scanning apparatus will have to be able to traverse the length of a container but it is possible that with improved scanning techniques that it will only need to move to one or more positions intermediate the length of the container or possibly could be fixed in position. In such a case, the second predetermined position could be a buffer deposition position on the front of the scanning apparatus trolley platform 41.

Reference is made to FIG. 3. The scanning apparatus 39 envisioned by the present invention includes a focused radiation emitter 47 housed in a shield 49 which directs radiation toward the container 43 suspended at the second predetermined position 33 as shown by the dotted lines. A receptive screen and radiation shield 51 are positioned behind the container and supported by the same reciprocating platform or trolley 41 which supports the radiation emitter and its shielding. The scanning apparatus support and trolley platform 41 also functions as a shield to prevent radiation from scattering downward in order to protect dockside workers and truck driver personnel located under the platform 27. A shield door 53 mounted on rollers can be provided under the scanning apparatus to cover the access door in the floor of the landing deck during scanning to prevent radiation from reaching the truck drivers and dock personnel.

The final step of the method comprises scanning containers during transfer between the first predetermined landing position and the third land predetermined landing position and while the containers are located at the second predetermined position during the container transfer cycle between the first and third predetermined positions. When a cargo container is transferred by the bridge crane from either the landside transportation (third predetermined position) or the quay crane (first predetermined) landing position 29 to the intended receiving deposition position, it is stopped during transit at the second predetermined position 33 and the nonintrusive scanning apparatus 39 moves along the length of the landing platform 27 to scan the suspended container 43 at the second predetermined position before it is either lowered onto the land transportation truck trailer chassis or moved to land on one of the buffer/landing (first predetermined) positions 29.

The presently available scanning apparatus 39 can include x-ray machines and gamma ray detectors, and eventually neutron analysis machines. These latter devices may not require the capability of moving along the container to scan it. Positioning it at one place in relation to the scanning apparatus may be sufficient and permit the container to be deposited on the landing deck at a buffer position while the scanning apparatus performs its function. In each case, radiation emission from the scanning apparatus either interrogates the containers or is detected by the scanning apparatus. So the term scanning apparatus includes all forms of radiation emissions generation and detection equipment used in the present invention. When new and improved noninvasive scanning equipment evolves, it can be substituted for the radiation emission generation or detection equipment with the deletion of the unnecessary radiation protective apparatus, and mounted on the translating platform. Modifications to the present apparatus are envisioned as coming within the concept and apparatus of the present invention as claimed.

The present invention provides a method of operation for a container scanning crane which can function as a buffer between two port operations and allows the other port operations to continue uninterrupted. Security scanning or screening occurs while a container is located in a buffer whereby the port operations continue to function without interruption. The scanning crane provides its own bridge crane for independent handling of the containers and includes a reciprocating trolley that is capable of moving the scanning apparatus along the length of a container which has been picked up by the scanning crane. The bridge crane positions the scanning apparatus above the dockside truck operations so that it does not interfere with the flow of trucks on the wharf. The scanning crane is an independent machine which can be installed in ports with minimum modifications to the facilities.

Thus it will be apparent from the foregoing description of the invention in its preferred form that it will fulfill all the objects and advantages attributable thereto. While it is illustrated and described in considerable detail herein, the invention is not to be limited to such details as have been set forth except as may be necessitated by the appended claims.

We claim:

1. A method for integrating nonintrusive scanning of cargo containers quay side, while they are being transferred between ship and land transportation by a quay crane, which does not interfere with the quay crane ship loading or unloading cycle operations, the steps comprising providing a mobile scanning platform mounted on tires and formed for independent movement of said platform on the wharf in a quay area whereby it can be located at variable positions below or adjacent to different container handling quay cranes on said wharf, said platform having at least a first predetermined container buffer landing position whereby said platform can be positioned under a quay crane and containers can be deposited onto or removed from said landing position by a quay crane, providing said platform with a bridge Crane mounted above said platform for transferring containers between said first predetermined landing position on said platform and a third predetermined position located below or alongside said platform where trailer trucks can be positioned, said bridge crane being capable of suspending a container at a second predetermined fixed position located at platform height between said first and third predetermined positions, providing a movable scanning inspection apparatus on said platform capable of traversing the length of a container located at said second predetermined position, and scanning containers while said containers are positioned at said suspended second predetermined position during transfer between said first and third predetermined landing positions in the container transfer cycle between a quay crane and shore.

2. The method for integrating nonintrusive scanning of cargo containers of claim 1 wherein providing said first predetermined position includes providing a multiple of buffer landing positions.

\* \* \* \* \*